United States Patent [19]

Chance et al.

[11] Patent Number: 4,652,547

[45] Date of Patent: Mar. 24, 1987

[54] PHARMACEUTICAL FORMULATIONS COMPRISING HUMAN INSULIN AND HUMAN PROINSULIN

[75] Inventors: Ronald E. Chance, Westfield; Bruce H. Frank; John A. Galloway, both of Indianapolis, all of Ind.

[73] Assignee: Eli Lilly and Company, Indianapolis, Ind.

[21] Appl. No.: 682,207

[22] Filed: Dec. 17, 1984

Related U.S. Application Data

[63] Continuation-in-part of Ser. No. 576,048, Feb. 1, 1984, abandoned, which is a continuation-in-part of Ser. No. 404,000, Aug. 2, 1982, abandoned, which is a continuation-in-part of Ser. No. 296,714, Aug. 27, 1981, abandoned.

[51] Int. Cl.$^4$ ............................................. A61K 37/26
[52] U.S. Cl. ........................................................ 514/4
[58] Field of Search ............................................. 514/4

[56] References Cited

U.S. PATENT DOCUMENTS 4,183,849  1/1980  Hansen et al. ...................... 424/178

FOREIGN PATENT DOCUMENTS 2105191  3/1983  United Kingdom .

OTHER PUBLICATIONS

Oyer, et al., J. Biol. Chem. 246, 1375–1386 (1971).
Yu, et al., J. Biol. Chem. 248, 3753–3761 (1973).
Horwitz, et al., J. Clin. Invest. 55, 1278–1283 (1975).
Kitabchi, *Metabolism* 26, 547–587 (1977).
Yanaihara, et al., *Diabetes* 27 (Suppl. 1), 149–160 (1978).
Yanaihara, et al., Characterization of Synthetic Human Proinsulin and C-Peptide, *Proinsulin, Insulin, C-Peptide* 41–49 (Excerpta Medica, 1979).
Rees, et al., *Diabetes* 18, 341 (1969).
Galloway, et al., *Diabetes* 18, 341 (1969).
Galloway, et al., *J. Lab. Clin. Med.* 78, 991–992 (1971).
Kitabchi, *South. Med. J.* 65, 833–838 (1972).
Low, et al., *Nature* 248, 339–340 (1974).
Starr, et al., *J. Clin. Endocrinol. Metab.* 38, 305–308 (1974).
Tompkins et al., *Diabetologia* 20, 94–101 (1981).
Fineberg, et al., *Diabetes* 22, 676–686 (1973).

*Primary Examiner*—Frederick E. Waddell
*Attorney, Agent, or Firm*—William C. Martens, Jr.

[57] ABSTRACT

A pharmaceutical composition which comprises, in association with a pharmaceutically acceptable carrier, human insulin and human proinsulin in a weight ratio, human insulin to human proinsulin, of from about 1:100 to about 100:1, is useful in treating diabetics and in promoting attainment of natural hormonal homeostasis, thereby preventing or substantially diminishing or retarding diabetic complications.

14 Claims, No Drawings

PHARMACEUTICAL FORMULATIONS COMPRISING HUMAN INSULIN AND HUMAN PROINSULIN

CROSS REFERENCE

This is a continuation-in-part of application Ser. No. 576,048 filed Feb. 1, 1984 and now abandoned, which is a continuation-in-part of application Ser. No. 404,000 filed Aug. 2, 1982, now abandoned, which is a continuation-in-part of application Ser. No. 296,714 filed Aug. 27, 1981, and now abandoned.

BACKGROUND OF THE INVENTION

Diabetes mellitus is a metabolic disorder characterized by the failure of body tissues to oxidize carbohydrates at the normal rate. Its most important factor is a deficiency of insulin. During the last 60 years people suffering from diabetes have been greatly aided by receiving controlled amounts of insulin. To the present time, the insulin used by diabetics has been isolated from animal pancreases, generally bovine and porcine. Both bovine and porcine insulin differ structurally from insulin generated by the human pancreas. Recently, it has become possible, by recombinant DNA methodology, to produce insulin identical to that produced by the human pancreas. The use of such insulin will enable the diabetic to more closely mimic the natural system than heretofore has been possible.

Nevertheless, it long has been recognized that administration of insulin to the diabetic is alone insufficient to restore and/or maintain the normal metabolic state. Although insulin has its manifested effect on carbohydrate metabolism, diabetes mellitus carries additional disorders, most if not all of which are related to the structure and function of blood vessels. The deficiencies leading to these disorders rarely are completely corrected by conventional insulin therapy.

Those vascular abnormalities associated with diabetes often are referred to as "complications of diabetes". They consist generally of microangiopathic changes resulting in lesions in the retina and the kidney. Neuropathy represents an additional diabetic complication which may or may not be related directly or indirectly to the noted microangiopathic changes. Examples of specific manifestations of diabetes complications are (1) diseases of the eye, including retinopathy, cataract formation, glaucoma, and extraocular muscle palsies; (2) diseases of the mouth, including gingivitis, increased incidence of dental caries, periodontal disease, and greater resorption of the alveolar bone; (3) motor, sensory, and autonomic neuropathy; (4) large-vessel disease; (5) microangiopathy; (6) diseases of the skin, including xanthoma diabeticorum, necrobiosis lipoidica diabeticorum, furunculosis, mycosis, and pruritis; (7) diseases of the kidneys, including diabetic glomerulosclerosis, arteriolar nephrosclerosis, and pyelonephritis; and (8) problems during pregnancy, including increased incidence of large babies, stillbirths, miscarriages, neonatal deaths, and congenital defects.

Many, and perhaps all, of the diabetic complications are the result of the failure of insulin alone to restore the body to its natural hormonal balance.

This invention is directed to pharmaceutical compositions and methods that more nearly achieve and maintain natural hormonal homeostasis in a diabetic state than can be achieved by administration of insulin alone.

SUMMARY OF THE INVENTION

Thus, this invention is directed to a pharmaceutical composition comprising, in association with a pharmaceutically acceptable carrier, human insulin and human proinsulin in a ratio on a weight basis, human insulin to human proinsulin, of from about 1:100 to about 100:1.

In addition, this invention is directed to a method for more nearly achieving and maintaining natural hormonal homeostasis in a diabetic state, which comprises administering, in association with a pharmaceutically acceptable carrier, pharmaceutically acceptable amounts of human insulin and human proinsulin in a ratio on a weight basis, human insulin to human proinsulin, of from about 1:100 to about 100:1.

DETAILED DESCRIPTION OF THE INVENTION

The two essential constituents of the pharmaceutical compositions of this invention and administered in accordance with the method of this invention are human insulin and human proinsulin.

The administration of a combination of human insulin and human proinsulin using a composition in accordance with this invention will produce a more natural utilization of glucose and better glucose control than is achieved by insulin alone, thereby diminishing hereinbefore described adverse diabetic complications.

Human proinsulin is available via a variety of routes, including organic synthesis, isolation from human pancreas by conventional methodology, and, more recently, recombinant DNA methodology.

In broad outline, the production of proinsulin using recombinant DNA methodology involves obtaining, whether by isolation, construction, or a combination of both, a sequence of DNA coding for the amino acid sequence of human proinsulin. The human proinsulin DNA then is inserted in reading phase into a suitable cloning and expression vehicle. The vehicle is used to transform a suitable microorganism after which the transformed microorganism is subjected to fermentation conditions leading to (a) the production of additional copies of the proinsulin gene-containing vector and (b) the expression of proinsulin or a proinsulin precursor product.

In the event the expression product is a proinsulin precursor, it generally will comprise the human proinsulin amino acid sequence joined at its amino terminal end to a fragment of a protein normally expressed in the gene sequence into which the proinsulin gene has been inserted. The proinsulin amino acid sequence is joined to the protein fragment through a specifically cleavable site, typically methionine. This product is customarily referred to as a fused gene product.

The proinsulin amino acid sequence is cleaved from the fused gene product using cyanogen bromide after which the cysteine sulfhydryl moieties of the proinsulin amino acid sequence are stabilized by conversion to their corresponding S-sulfonates.

The resulting proinsulin S-sulfonate is purified, and the purified proinsulin S-sulfonate then is converted to proinsulin by formation of the three properly located disulfide bonds. The resulting proinsulin product is purified.

Human insulin also is available via a variety of routes, including organic synthesis, isolation from human pancreas by conventional techniques, conversion of isolated animal insulin, conversion of human proinsulin, and recombinant DNA methodology.

Human proinsulin, however produced, can be enzymatically cleaved, for example, using trypsin and carboxypeptidase B, to produce human insulin.

Using recombinant DNA methodology in a manner analogous to that hereinbefore described for the production of human proinsulin, human insulin can be prepared by the separate expression and isolation of human insulin A-chain and human insulin B-chain followed by their proper disulfide bond formation.

Human insulin can also be prepared from porcine insulin. Human insulin differs from porcine insulin by a single amino acid, i.e., the B-chain carboxyl terminal amino acid. Alanine, the B-30 amino acid of porcine insulin, is cleaved and replaced by threonine. In this regard, see, for example, U.S. Pat. No. 3,276,961.

The compositions of this invention contain both human insulin and human proinsulin. They are present in a weight ratio, human insulin to human proinsulin, of from about 1:100 to about 100:1. Preferably, the weight ratio of human insulin to human proinsulin is from about 1:2 to about 100:1, more preferably, from about 1:1 to about 20:1, and, most preferably, from about 4:1 to about 20:1. Additional preferred weight ratio ranges, human insulin to human proinsulin, are from about 1:30 to about 100:1; from about 1:15 to about 100:1; from about 1:10 to about 100:1; from about 1:30 to about 20:1; from about 1:15 to about 20:1; and from about 1:10 to about 20:1.

As noted, the compositions and methods of this invention are useful in promoting the attainment of natural hormonal homeostasis and thereby preventing or substantially diminishing or retarding those recognized diabetic complications.

It is recognized that certain diabetics are unable to effectively receive insulin by subcutaneous injection due to the presence of proteases at the injection site that rapidly destroy the insulin before it has an opportunity to be absorbed into the bloodstream and transported to the receptor sites. These diabetics, if they are to receive insulin at all, must receive it by intravenous injection. The necessary repeated intravenous injections are undesirable due to their deleterious effect on the veins of the recipient and infections associated therewith. It has been discovered that human proinsulin is not degraded by these insulin-degrading proteases and, thus, it can be administered by subcutaneous injection. Its stability and thus availability promote attainment of natural hormonal homeostasis. Moreover, since insulin and proinsulin together form complexes, it can be expected that proinsulin will afford protection for the otherwise degradable insulin.

It also has been noted from recent studies [Podlecki et al., *Diabetes*, 31, Suppl. 2, 126A (1982)] that human proinsulin is internalized into target tissues, e.g., fat cells. Although its particular intracellular action on a molecular scale is as yet undetermined, these findings further support the disclosure herein that human proinsulin plays an active role in and is necessary for the attainment of natural hormonal homeostasis.

Schluter et al., *Diabetes* 31, Suppl. 2, 135A (1982), describe studies that demonstrate that human insulin receptor binding is enhanced by the presence of human proinsulin. These results again further support the disclosure herein that the availability and presence of human proinsulin results in the promotion or restoration of natural hormonal homeostasis.

In addition to promoting the attainment of natural hormonal homeostasis, those compositions of this invention in which the weight ratio, human insulin to human proinsulin, is equal to or less than about 1:1, afford the added benefit of an extra long hypoglycemic effect. Preferred compositions which carry this added benefit have a weight ratio, human insulin to human proinsulin, of from about 1:100 to about 1:1. Other preferred weight ratios, human insulin to human proinsulin, are from about 1:30 to about 1:1, and, more particularly, from about 1:30 to about 1:10, or from about 1:10 to about 1:1. Such compositions will minimize the need for customary insulin formulation additives such as protamine which is present in NPH insulin or excess zinc which is present in Lente insulin. Both such additives are artificial and unphysiologic.

The amount of the compositions of this invention necessary to maintain natural hormonal homeostasis or to achieve a state that more nearly approaches natural hormonal homeostasis in the diabetic, of course, will depend upon the severity of the diabetic condition. Moreover, the amount will vary depending upon the route of administration. Ultimately, the amount of composition administered and the frequency of such administration will be at the discretion of the particular physician. In general, however, the dosage will be in the range affording from about 0.02 to about 5 units of human insulin activity per kilogram body weight per day, and, preferably, from about 0.1 to about 1 unit of human insulin activity per kilogram body weight per day.

The composition is administered parenterally, including subcutaneous, intramuscular, and intravenous. The compositions of this invention comprise the active ingredients, human insulin and human proinsulin, together with a pharmaceutically acceptable carrier therefor and, optionally, other therapeutic ingredients. The carrier must be acceptable in the sense that it is compatible with other components of the composition and is not deleterious to the recipient thereof.

Compositions of this invention suitable for parenteral administration conveniently comprise sterile aqueous solutions and/or suspensions of the pharmaceutically active ingredients, which solutions or suspensions preferably are made isotonic with the blood of the recipient, generally using sodium chloride, glycerin, glucose, mannitol, sorbitol, and the like.

In addition, the compositions may contain any of a number of adjuvants, such as buffers, preservatives, dispersing agents, agents that promote rapid onset of action, agents that promote prolonged duration of action, and the like. Typical preservatives are, for example, phenol, m-cresol, methyl p-hydroxybenzoate, and the like. Typical buffers are, for example, sodium phosphate, sodium acetate, sodium citrate, and the like.

Moreover, an acid, such as hydrochloric acid, or a base, such as sodium hydroxide, can be used for pH adjustment. In general, the pH of the aqueous composition ranges from about 2 to about 8, and, preferably, from about 6.8 to about 8.0.

Other suitable additives are, for example, divalent zinc ion, which, if present at all, is generally present in an amount from about 0.01 mg. to about 0.5 mg. per 100 units of human insulin, and protamine salt (for example, in the form of its sulfate), which, if present at all, is generally present in an amount from about 0.1 mg. to about 3 mg. per 100 units of human insulin activity.

Examples of particular pharmaceutical compositions of this invention are provided in the examples appearing hereinbelow.

EXAMPLE 1

Neutral Regular Human Insulin: Human Proinsulin Formulation [100:1 human insulin:human proinsulin on weight basis at 40 Units (U) insulin per cubic centimeter (cc.)]

To prepare 10 cc. of the composition, mix

| | |
|---|---|
| Human Zinc Insulin (28 U/mg.) | 400 U |
| Human Proinsulin | 0.14 mg. |
| Phenol, distilled | 20 mg. |
| Glycerin | 160 mg. |

Water and either 10% hydrochloric acid or 10% sodium hydroxide sufficient to make a composition volume of 10 cc. and a final pH of 7.0–7.8.

EXAMPLE 2

Neutral Regular Human Insulin:Human Proinsulin Formulation [20:1 human insulin:human proinsulin on weight basis at 100 U insulin per cc.]

To prepare 10 cc. of the composition, mix

| | |
|---|---|
| Human Zinc Insulin (28 U/mg.) | 1000 U |
| Human Proinsulin | 1.8 mg. |
| Phenol, distilled | 20 mg. |
| Glycerin | 160 mg. |

Water and either 10% hydrochloric acid or 10% sodium hydroxide sufficient to make a composition volume of 10 cc. and a final pH of 7.0–7.8.

EXAMPLE 3

Protamine, Zinc Human Insulin:Human Proinsulin Formulation [20:1 human insulin:human proinsulin on weight basis at 40 U insulin per cc.]

To prepare 10 cc. of the composition, mix

| | |
|---|---|
| Human Zinc Insulin (28 U/mg.) | 400 U |
| Human Proinsulin | 0.7 mg. |
| Phenol, distilled | 25 mg. |
| Zinc Oxide | 0.78 mg. |
| Glycerin | 160 mg. |
| Protamine Sulfate | 4.0–6.0 mg. |
| Sodium Phosphate, crystals | 38 mg. |

Water and either 10% hydrochloric acid or 10% sodium hydroxide sufficient to make a composition volume of 10 cc. and a final pH of 7.1–7.4.

EXAMPLE 4

Protamine, Zinc Human Insulin:Human Proinsulin Formulation [1:1 human insulin:human proinsulin on weight basis at 100 U insulin per cc.]

To prepare 10 cc. of the composition, mix

| | |
|---|---|
| Human Zinc Insulin (28 U/mg.) | 1000 U |
| Human Proinsulin | 36 mg. |
| Phenol, distilled | 25 mg. |
| Zinc oxide | 2.0 mg. |
| Glycerin | 160 mg. |
| Protamine Sulfate | 10–15 mg. |
| Sodium Phosphate, crystals | 38 mg. |

Water and either 10% hydrochloric acid or 10% sodium hydroxide sufficient to make a composition volume of 10 cc. and a final pH of 7.1–7.4.

EXAMPLE 5

Isophane Protamine, Zinc Human Insulin:Human Proinsulin Formulation [4:1 human insulin:human proinsulin on weight basis at 40 U insulin per cc.]

To prepare 10 cc. of the composition, mix

| | |
|---|---|
| Human Zinc Insulin (28 U/mg.) | 400 U |
| Human Proinsulin | 3.6 mg. |
| m-Cresol, distilled | 16 mg. |
| Phenol, distilled | 6.5 mg. |
| Glycerin | 160 mg. |
| Protamine Sulfate | 1.2–2.4 mg. |
| Sodium Phosphate, crystals | 38 mg. |

Water and either 10% hydrochloric acid or 10% sodium hydroxide sufficient to make a composition volume of 10 cc. and a final pH of 7.1–7.4.

EXAMPLE 6

Isophane Protamine, Zinc Human Insulin:Human Proinsulin Formulation [1:2 human insulin:human proinsulin on weight basis at 100 U insulin per cc.]

To prepare 10 cc. of the composition, mix

| | |
|---|---|
| Human Zinc Insulin (28 U/mg.) | 1000 U |
| Human Proinsulin | 71 mg. |
| m-Cresol, distilled | 16 mg. |
| Phenol, distilled | 6.5 mg. |
| Glycerin | 160 mg. |
| Protamine Sulfate | 3.0–6.0 mg. |
| Sodium Phosphate, Crystals | 38 mg. |

Water and either 10% hydrochloric acid or 10% sodium hydroxide sufficient to make a composition volume of 10 cc. and a final pH of 7.1–7.4.

EXAMPLE 7

Zinc Human Insulin Suspension:Human Proinsulin Formulation [1:10 human insulin:human proinsulin on weight basis at 40 U insulin per cc.]

To prepare 10 cc. of the composition, mix

| | |
|---|---|
| Human Zinc Insulin (28 U/mg.) | 400 U |
| Human Proinsulin | 143 mg. |
| Sodium Acetate, Anhydrous | 16 mg. |
| Sodium Chloride, Granular | 70 mg. |
| Methyl p-Hydroxybenzoate | 10 mg. |
| Zinc Oxide | 0.63 mg. |

Water and either 10% hydrochloric acid or 10% sodium hydroxide sufficient to make a composition volume of 10 cc. and a final pH of 7.2–7.5.

EXAMPLE 8

Zinc Human Insulin Suspension:Human Proinsulin Formulation [20:1 human insulin:human proinsulin on weight basis at 100 U insulin per cc.]

To prepare 10 cc. of the composition, mix

| | |
|---|---|
| Human Zinc Insulin (28 U/mg.) | 1000 U |
| Human Proinsulin | 1.8 mg. |
| Sodium Acetate, Anhydrous | 16 mg. |
| Sodium Chloride, Granular | 70 mg. |
| Methyl p-Hydroxybenzoate | 10 mg. |
| Zinc Oxide | 1.6 mg. |

Water and either 10% hydrochloric acid or 10% sodium hydroxide sufficient to make a composition volume of 10 cc. and a final pH of 7.2–7.5.

EXAMPLE 9

Neutral Regular Human Insulin:Human Proinsulin Formulation [100:1 human insulin:human proinsulin on weight basis at 40 U insulin per cc.]

To prepare 10 cc. of the composition, mix

| | |
|---|---|
| Human Sodium Insulin (28 U/mg.) | 400 U |
| Human Proinsulin | 0.14 mg. |
| Phenol, distilled | 20 mg. |
| Glycerin | 160 mg. |

Water and either 10% hydrochloric acid or 10% sodium hydroxide sufficient to make a composition volume of 10 cc. and a final pH of 7.0–7.8.

EXAMPLE 10

Neutral Regular Human Insulin:Human Proinsulin Formulation [20:1 human insulin:human proinsulin on weight basis at 100 U insulin per cc.]

To prepare 10 cc. of the composition, mix

| | |
|---|---|
| Human Sodium Insulin (28 U/mg.) | 1000 U |
| Human Proinsulin | 1.8 mg. |
| Phenol, distilled | 20 mg. |
| Glycerin | 160 mg. |

Water and either 10% hydrochloric acid or 10% sodium hydroxide sufficient to make a composition volume of 10 cc. and a final pH of 7.0–7.8.

Biological Actions of Human Proinsulin

A. Human Proinsulin—Peripheral vs. Hepatic Effect

Ten healthy control subjects (five female and five male) ranging in age from 25–40 years (mean age=29±3 years) with mean relative body weights of 0.96+0.02 were used. Prior to each study period each subject consumed a weight-maintaining diet containing 45% carbohydrate, 40% fat and 15% protein for at least 72 hours.

In vivo sensitivity to human insulin or human proinsulin was measured using a modification of the euglycemic glucose-clamp technique as described by DeFronzo, R. A., Tobin, J. D. and Andres, R., *Am. J. Physiol.* 237:E214–E223 (1979). With this technique, an antecubital vein is cannulated in an antegrade manner to administer the infusates. A dorsal hand vein is cannulated in a retrograde fashion and kept in a warming device (70° C.) to facilitate venous sampling and provide arterialized venous blood. After insertion of the catheters, [3—3H]-glucose is infused for at least 30 minutes before initiating the hormone infusion. At the onset of hormone infusion, a priming dose of either insulin or proinsulin is administered during the initial 10 minutes in a logarithmically decreasing manner to acutely raise the serum hormone level. The amount of insulin or proinsulin given during this initial 10 minute period is roughly twice that given during each subsequent 10 minute interval by a continuous hormone infusion. The serum glucose is maintained between 80 and 90 mg/dl throughout the study period with a coefficient of variation of less than 5% by means of a variable rate of infusion of 20% dextrose. The overall glucose disposal rate is assessed isotopically for each 20 minute interval of the study.

To determine the length of time required to reach a steady state biological effect with human insulin or human proinsulin infusions, initial studies were performed in 5 subjects. On one day, each subject received a 5.0 µg/M2/min (120 mU/M2/min) insulin infusion over a 6 hour period. On another day, each subject received a 22.5 µg/M2/min proinsulin infusion over an 8 hour period. Steady state rates of glucose disposal were reached by 3 and 5 hours with insulin and proinsulin respectively. Based on these results, during all subsequent studies, insulin was infused for 180 minutes and its biological effects were assessed using the data from the 3rd hour of each study. Each proinsulin infusion was carried out for 300 minutes, with the quantitation of its biological effects based on measurements made during the 5th hour of each study. The data for the last three 20 minute intervals of each study were subsequently meaned and used as the data point for that particular study.

Each subject underwent a total of 8 euglycemic glucose clamp studies, each performed on a separate day. Insulin infusion rates of 15, 40, 120, and 240 mU/M2/min were utilized to construct a dose response curve for insulin action. With this approach an attempt was made to achieve steady state insulin concentrations of 40 to 800 µU/ml (Table 1). Each subject was also studied with four different proinsulin infusions. The proinsulin infusion rates chosen (2.75, 7.5, 22.5 and 45.0 µg/M2/min) were designed to achieve steady state hormone levels of ~3–50 pmol/ml, or roughly ten times greater than insulin on a molar basis (Table 1). In order to simplify comparison of the biological effects of human insulin and human proinsulin, these infusion rates are designated as infusions A, B, C, and D, respectively, with the hormone infusion rate increasing in alphabetical order. Hepatic glucose output was quantitated in the basal state and during each clamp study using a primed continuous infusion of [3—3H]glucose. The mean basal rate of hepatic glucose output was 87±3 mg/M2/min. The dose response relationship for insulin and proinsulinmediated suppression of hepatic glucose output was determined by calculating the percent suppression of basal hepatic glucose output at each steady state hormone concentration obtained during the euglycemic clamp studies. Much higher serum concentrations of proinsulin were required to achieve a comparable degree of hepatic glucose output suppression. For example, to achieve 90% suppression, a proinsulin concentration of 3.35 pmol/ml was required compared to an insulin concentration of 0.38 pmol/ml. Comparisons of several different insulin and proinsulin concentrations demonstrated that on a molar basis, proinsulin has ~12% the potency of insulin in suppressing hepatic glucose output.

As shown in Table 2 following, the relative biologic potency of human proinsulin to suppress hepatic glucose output is greater than its effect to stimulate glucose disposal. During Study A, the proinsulin infusion yielded serum levels ten times greater than the corresponding insulin infusion (Table 1). As shown in Table 2, hepatic glucose output was suppressed by a comparable degree during both infusions. In contrast, glucose disposal rates measured during the proinsulin infusion were only 70% of those achieved during the insulin infusions ($p<0.01$). Thus, during study A, the concentrations of proinsulin and insulin achieved yielded comparable effects to inhibit hepatic glucose production but proinsulin was only 70% as effective in stimulating glucose disposal.

TABLE 1

INSULIN AND PROINSULIN INFUSION RATES DURING EUGLYCEMIC CLAMP STUDIES AND STEADY STATE HORMONE LEVELS ACHIEVED

|  | A | B | C | D |
|---|---|---|---|---|
| Hormone Infusions: |  |  |  |  |
| Insulin (mU/M$^2$/min) | 15 | 40 | 120 | 240 |
| Insulin ($\mu$g/M$^2$/min) | 0.63 | 1.67 | 5.0 | 10.0 |
| Proinsulin ($\mu$g/M$^2$/min) | 2.75 | 7.5 | 22.5 | 45.0 |
| Steady State Hormone Levels (Mean ± SEM): |  |  |  |  |
| Insulin ($\mu$U/ml) | 37 ± 3 | 93 ± 7 | 291 ± 14 | 800 ± 65 |
| Insulin (pmol/ml) | 0.26 ± 0.02 | 0.66 ± 0.05 | 2.09 ± 0.10 | 5.25 ± 0.47 |
| Proinsulin (pmol/ml) | 2.55 ± 0.16 | 6.24 ± 0.49 | 21.2 ± 1.4 | 40.0 ± 1.9 |

TABLE 2

PERIPHERAL VS HEPATIC EFFECTS OF HORMONE INFUSIONS DURING STUDY A

|  | (Mean ± SE) | |
|---|---|---|
|  | Insulin | Proinsulin |
| Suppression of Hepatic Glucose Output (%) | 82 ± 6 | 80 ± 6 |
| Glucose Disposal Rate (mg/M$^2$/min) | 176 ± 17 | 122 ± 11* |

*$p<0.01$

B. Kinetics of Activation and Deactivation of the Biologic Effects of Human Proinsulin on Peripheral Glucose Uptake and Hepatic Glucose Output (HGO)

The kinetics of activation and deactivation of human proinsulin's biologic effects on peripheral glucose uptake and hepatic glucose output (HGO) in comparison to human insulin were studied. At all infusion rates, when human insulin was infused in a primed continuous manner, an initial peak of the human insulin concentration was noted after 5-10 minutes and steady state human insulin concentrations were achieved after approximately 20 minutes. In contrast, when human proinsulin was infused in this manner, no initial peak of hormone concentration was observed and steady state levels were not achieved until 90-120 minutes. Thus, the initial volume of distribution was different for human proinsulin (much greater), and the time to reach steady state concentration was longer. This latter finding is only partially explained by the lower metabolic clearance rate (MCR) for human proinsulin compared to that of human insulin.

Marked differences between the two hormones were noted when biologic activity was studied. For example, the time needed to reach steady state biologic effects was much slower for human proinsulin compared to human insulin, for both stimulation of glucose disposal and inhibition of HGO. Thus, human insulin's effects to stimulate glucose disposal reached steady state after 2-3 hours. In contrast, steady state biologic effects of human proinsulin on glucose disposal were not achieved until after 5 hours. This marked prolongation of the activation kinetics of human proinsulin is only partially explained by the longer time to reach steady state hormone levels. This indicates a difference in human proinsulin's cellular action such that its activation kinetics are markedly slower than those of human insulin. A likely mechanism for this effect can be based upon the finding that the association rate constant for human proinsulin binding to cellular receptors is only 10% as great as the association rate constant for human insulin binding to receptors.

A most striking and important finding concerning the kinetics of human proinsulin action relates to its rate of deactivation. These studies were performed by infusing human insulin and human proinsulin (0.55 $\mu$g/M$^2$/min and 2.75 $\mu$g/M$^2$/min, respectively) for 5 hours, at which time steady state biologic effects to stimulate glucose disposal and inhibit HGO were achieved. At this point, the hormone infusion was abruptly stopped, and the glucose concentration was maintained constant until the biologic effects of the infused hormone were no longer detectable. The results showed that both hormones were rapidly cleared from the circulation. The t ½ for human insulin was 5-7 minutes whereas the t ½ for human proinsulin was 20 minutes. Although the t ½ for human proinsulin was greater than that for human insulin, both hormones disappeared quite rapidly relative to the dissipation of biologic effects. Deactivation of human insulin's effects on glucose disposal proceeded with a t ½ of 41±6 minutes whereas deactivation of human proinsulin's effects on glucose disposal proceeded with a t ½ of 87±14 minutes, and glucose disposal rates did not return to basal until 160 minutes following cessation of the human proinsulin infusion. Thus, compared to human insulin, human proinsulin's biologic effect to stimulate glucose disposal decays 2.2 times more slowly. It should be noted that in these experiments both hormones are cleared from the circulation relatively rapidly, and hormone concentrations are below biologically effective values by 20 minutes for human insulin and 90 minutes for human proinsulin. The most notable feature of these studies relates to human proinsulin's effect to suppress HGO. When the decay of human insulin's effect to inhibit HGO was assessed, it was found that human insulin's action deactivated with a t ½ of 49±8 minutes and HGO values returned to baseline after approximately 120 minutes. In marked contrast, when human proinsulin infusions were stopped, no decline in human proinsulin's effects to suppress HGO could be detected until 120 minutes, and deactivation proceeded with t ½ of 230±19 minutes. The experiments could not be carried out long enough to determine when human proinsulin's effects were completely gone, but extrapolation of the curve would indicate that HGO did not return to baseline values until after 6 hours. It should be recalled that the hormone is effectively completely removed from the circulation after 90 minutes, yet half of its biologic effects on HGO persists for 4 hours with additional effects persisting for at least 2 more hours. This is a key observation and demonstrates a new aspect of human proinsulin action, underscoring its marked hepatic potency to suppress glucose production. Thus, not only does human proinsulin have greater effects on the liver than on the periphery, but these effects are persistant and long lasting even after hormone concentrations have declined in plasma. This is highly significant in terms of human proinsulin's clinical importance.

A most important observation made from these investigations is human proinsulin's markedly prolonged rate of deactivation on HGO. Coupled with human proinsulin's greater potency on HGO versus peripheral glucose disposal, a therapeutic role for human proinsulin in the treatment of diabetes is readily visualized. For example, in non-insulin dependent diabetes mellitus (NIDDM), one of the major metabolic abnormalities that maintains the resultant hyperglycemic state is accelerated hepatic glucose production. Based on this finding and others regarding human proinsulin's biologic effects, it is evident that if human proinsulin were given so as to achieve a circulating concentration of approximately 1.5 2 pmol/ml, the HGO would be suppressed approximately 50% in NIDDM subjects. From earlier studies in NIDDM, it can be calculated that this would reduce HGO into the normal range. The findings regarding human proinsulin deactivation indicate that once the biologic effect of this concentration of human proinsulin was fully expressed, it would be largely maintained for several hours. A major advantage of this approach is that this level of human proinsulin will have little if any effect on peripheral glucose disposal, even though HGO would be suppressed by about 50%. Since glucose disposal will not be appreciably stimulated by this concentration of human proinsulin, there is little possibility that hypoglycemia could develop.

Using the above line of reasoning, if human proinsulin were administered either by continuous subcutaneous insulin infusion (CSII) or by a single subcutaneous injection so as to achieve a sustained human proinsulin level of 1.5-2 pmol/ml for about 3 hours, then one would expect the HGO to be suppressed by about 50% and the plasma glucose level to fall to a therapeutically acceptable range with minimal possibility of hypoglycemia. Furthermore, based on the deactivation kinetics of human proinsulin's effect on HGO, one would also expect the HGO to remain suppressed and the plasma glucose to remain at an acceptable level for several hours. Such a mode of therapy could produce adequate glycemic control for 8-10 hours. Thus, a number of ways are available by which human proinsulin can be used in combination with diet, oral agents, or insulin in treating NIDDM. For example, human proinsulin can be administered at night to maintain glycemic control without fear of hypoglycemia so that fasting glucose levels will be acceptable in the morning. In addition to this, diet, oral agents, or even day time insulin, can then be used to maintain control during the day, with human proinsulin being used again at night.

Similar approaches are available for the Type I diabetic patient, although it is probable that simultaneous insulin therapy will also be necessary. In these patients, because of human proinsulin's potent and long lasting effects on HGO, a combination of human insulin and human proinsulin therapy will serve to lower insulin requirements and, more importantly, will smooth out insulin's effects on glycemic control. Thus, there would be less marked swings in blood glucose levels leading to much easier control in Type I diabetic patients on one or two insulin injections per day. In those Type I diabetic patients on CSII therapy, the total human proinsulin-equivalent plus insulin levels to which tissues are exposed would be lower. This is important in view of the hyperinsulinemia which is present in well controlled patients on CSII.

C. Restoration to Euglycemia (Hormonal Homeostasis) Using Human Proinsulin

To five non-insulin dependent diabetes mellitus (Type II) subjects were administered subcutaneously at 7:00 a.m. on separate days either 0.2 U/kg human insulin or 0.2 U/kg human proinsulin. The actual administered amounts were based upon an insulin activity of 28 IU/mg and a proinsulin activity of 4 IU/mg.

Following injection of human insulin, the mean peak insulin blood level for the five subjects was 0.6 pmol/ml (97 $\mu$U/ml) at 140±13 minutes whereas, following injection of human proinsulin, the mean peak proinsulin blood level was 6.8 pmol/ml at 230±33 minutes.

The basal hepatic glucose production in the Type II subjects was elevated (3.83±0.6 mg/kg/min in the Type II subjects vs. 2.05±0.24 mg/kg/min in normals). Following human proinsulin administration, the hepatic glucose production in the Type II subjects was suppressed into the normal range, with maximum effect and minimum glucose production of 1.21±0.2 mg/kg/min by 264±31 minutes. Administration of human insulin likewise suppressed hepatic glucose production to the normal range; however, a quicker onset was seen, with the maximum suppression being reached by 168 minutes.

The startling and wholly unexpected discovery regarding human proinsulin relative to human insulin is apparent from an examination of the blood glucose levels available from administration of each. These are seen in Tables 3 and 4 following. Table 3 shows the effects from administering 0.2 U/kg of regular human insulin subcutaneously. By approximately 300 minutes following injection, three of the five subjects had experienced hypoglycemia, and restorative measures had to be initiated. It is noteworthy that one of the three hypoglycemic subjects had, initially, the highest blood glucose level. Of the remaining two subjects, one very nearly experienced hypoglycemia, reaching a minimum of 74 mg/dl blood glucose at 240 minutes following injection.

In contradistinction, Table 4 provides the results from administration of human proinsulin. Not only was hypoglycemia nowhere evidenced but the blood glucose level of each subject was lowered to a normal range (about 80-110 mg/dl) and remained in the such normal range for an extended period.

TABLE 3

THE RESPONSE OF FIVE FASTING TYPE II DIABETIC PATIENTS TO NEUTRAL REGULAR HUMAN INSULIN 0.2 U/KG S.C.

| Subject | Total Dose (I.U.) | Plasma Glucose (mg/dl) Time Elapsed After Injection (Minutes) | | | | | | | | | | | |
|---|---|---|---|---|---|---|---|---|---|---|---|---|---|
| | | 0 | 40 | 80 | 120 | 160 | 200 | 240 | 280 | 300 | 320 | 360 | 400 |
| RJW | 27.2 | 172 | 158 | 138 | 121 | 98 | 84 | 74 | 92 | — | 97 | 99 | — |
| DED | 20.0 | 230 | 218 | 208 | 192 | 175 | 166 | 148 | 145 | — | 141 | 137 | 136 |
| IST | 16.3 | 266 | 260 | 238 | 206 | 178 | 141 | 108 | 77 | 66 | Hypoglycemic | | |
| CCC | 14.8 | 226 | 216 | 197 | 168 | 120 | 72 | Hypoglycemic | | | | | |
| CAR | 15.0 | 298 | 280 | 212 | 118 | 60 | | Hypoglycemic | | | | | |
| Mean | 18.7 | 238 | 226 | 199 | 161 | 126 | — | — | — | — | — | — | — |

TABLE 4

THE RESPONSE OF FIVE FASTING TYPE II DIABETIC PATIENTS TO NEUTRAL REGULAR HUMAN PROINSULIN 0.2 U/KG S.C.

| Subject | Total Dose (I.U.) | Plasma Glucose (mg/dl) Time Elapsed After Injection (Minutes) | | | | | | | | | | | | | | |
|---|---|---|---|---|---|---|---|---|---|---|---|---|---|---|---|---|
| | | 0 | 40 | 80 | 120 | 160 | 200 | 240 | 280 | 300 | 320 | 360 | 400 | 440 | 480 | 500 |
| RJW | 27.2 | 159 | 144 | 138 | 128 | 118 | 110 | 101 | 98 | 88 | — | 84 | 85 | 86 | 88 | — |
| DED | 20.0 | 231 | 217 | 201 | 191 | 182 | 172 | 164 | 143 | 134 | — | 128 | 117 | 112 | 104 | 100 |
| IST | 16.3 | 290 | 282 | 272 | 250 | 230 | 200 | 183 | 152 | 127 | — | 101 | 82 | 77 | — | — |
| CCC | 14.8 | 213 | 203 | 187 | 168 | 140 | 108 | 81 | 77 | 80 | 80 | — | — | — | — | — |
| CAR | 15.0 | 332 | 328 | 308 | 288 | 272 | 247 | 210 | 174 | 137 | — | 94 | — | — | — | — |
| Mean | 18.7 | 245 | 235 | 221 | 205 | 188 | 167 | 148 | 129 | 113 | — | 102 | 95 | 92 | 96 | — |

We claim:

1. A method for more nearly achieving and maintaining natural hormonal homeostasis in a diabetic state, which comprises administering, in association with a pharmaceutically acceptable carrier, pharmaceutically acceptable amounts of human insulin and human proinsulin in a ratio on a weight basis, human insulin to human proinsulin, of from about 1:100 to about 100:1.

2. Method of claim 1, in which the weight ratio of human insulin to human proinsulin is from about 1:10 to about 100:1.

3. Method of claim 2, in which the weight ratio of human insulin to human proinsulin is from about 1:2 to about 100:1.

4. Method of claim 2, in which the weight ratio of human insulin to human proinsulin is from about 1:1 to about 20:1.

5. Method of claim 2, in which the weight ratio of human insulin to human proinsulin is from about 4:1 to about 20:1.

6. Method of claim 1, in which the weight ratio of human insulin to human proinsulin is from about 1:30 to about 100:1.

7. Method of claim 1, in which the weight ratio of human insulin to human proinsulin is from about 1:15 to about 100:1.

8. Method of claim 1, in which the weight ratio of human insulin to human proinsulin is from about 1:30 to about 20:1.

9. Method of claim 1, in which the weight ratio of human insulin to human proinsulin is from about 1:15 to about 20:1.

10. Method of claim 1, in which the weight ratio of human insulin to human proinsulin is from about 1:10 to about 20:1.

11. Method of claim 1, in which the weight ratio of human insulin to human proinsulin is from about 1:100 to about 1:1.

12. Method of claim 1, in which the weight ratio of human insulin to human proinsulin is from about 1:30 to about 1:1.

13. Method of claim 1, in which the weight ratio of human insulin to human proinsulin is from about 1:30 to about 1:10.

14. Method of claim 1, in which the weight ratio of human insulin to human proinsulin is from about 1:10 to about 1:1.

* * * * *